(12) United States Patent
Robran

(10) Patent No.: US 11,660,225 B2
(45) Date of Patent: May 30, 2023

(54) MODULAR KNEE EXTENSION DEVICE

(71) Applicant: Bone Foam, Inc., Corcoran, MN (US)

(72) Inventor: Chad Robran, Plymouth, MN (US)

(73) Assignee: Bone Foam, Inc., Corcoran, MN (US)

( * ) Notice: Subject to any disclaimer, the term of this patent is extended or adjusted under 35 U.S.C. 154(b) by 56 days.

(21) Appl. No.: 16/979,156

(22) PCT Filed: Mar. 6, 2019

(86) PCT No.: PCT/US2019/021047
§ 371 (c)(1),
(2) Date: Sep. 8, 2020

(87) PCT Pub. No.: WO2019/173537
PCT Pub. Date: Sep. 12, 2019

(65) Prior Publication Data
US 2020/0397608 A1    Dec. 24, 2020

Related U.S. Application Data

(60) Provisional application No. 62/639,661, filed on Mar. 7, 2018.

(51) Int. Cl.
*A61F 5/00* (2006.01)
*A61F 5/042* (2006.01)

(52) U.S. Cl.
CPC .................. *A61F 5/042* (2013.01)

(58) Field of Classification Search
CPC .. A61F 5/042; A61F 5/05; A61F 5/058; A61F 5/05841; A61F 5/0585; A61F 5/37; A61F 5/3761; A61F 5/3769; A61G 13/12; A61G 13/1205; A61G 13/123; A61G 13/1245; A61G 13/125; A61G 13/128; A61G 13/1285; A61G 13/1295;
(Continued)

(56) References Cited

U.S. PATENT DOCUMENTS 3,162,486 A * 12/1964 Emery ................... A47C 16/02
                                                          297/423.41
3,333,286 A *  8/1967 Biolik ...................... A47G 9/10
                                                                 5/632

(Continued)

FOREIGN PATENT DOCUMENTS

WO     WO2001012021      2/2001

OTHER PUBLICATIONS

International Search Report issued in PCT/US2019/021047 dated May 10, 2019.

*Primary Examiner* — Adam Baker
(74) *Attorney, Agent, or Firm* — Workman Nydegger (57) ABSTRACT

A modular device is configured to provide different levels of knee extension to a patient by being moveable between an assembled or "rest" configuration and a detached or "therapy" configuration. The device includes a proximal section with an inclined upper surface and a separate distal section with an inclined upper surface. When attached, the proximal and distal sections form a single continuous incline for supporting a patient's leg. At least one of the sections also includes an ankle supporting cavity that holds the patient's ankle and heel and provides greater stretching/extension of the patient's knee.

15 Claims, 6 Drawing Sheets

(58) Field of Classification Search
CPC ...... A61G 7/065; A61G 7/075; A61G 7/0755; A47C 16/02
USPC ........................................................ 128/845
See application file for complete search history.

(56) References Cited

U.S. PATENT DOCUMENTS

| | | | | |
|---|---|---|---|---|
| 3,568,671 | A | * | 3/1971 | Graham ................ A61F 5/0585 602/23 |
| 3,946,451 | A | * | 3/1976 | Spann .................. A61G 7/0755 5/650 |
| 3,995,846 | A | | 12/1976 | Frick |
| 5,584,303 | A | * | 12/1996 | Walle ......................... A61F 5/01 128/882 |
| 5,742,963 | A | * | 4/1998 | Trevino .................... A61G 1/00 128/845 |
| 5,997,491 | A | * | 12/1999 | Harris .................. A47C 20/021 128/882 |
| 2003/0182727 | A1 | * | 10/2003 | DuDonis .............. A61G 7/0755 5/648 |
| 2010/0319707 | A1 | * | 12/2010 | Cardin ................. A61G 7/0755 128/845 |
| 2012/0180219 | A1 | * | 7/2012 | Riccabona ........... A47C 20/021 5/636 |
| 2016/0184126 | A1 | | 6/2016 | Boezaart et al. |
| 2017/0281446 | A1 | | 10/2017 | Parsell et al. |
| 2018/0008499 | A1 | | 1/2018 | Lucey et al. |

* cited by examiner

MODULAR KNEE EXTENSION DEVICE

BACKGROUND

Following injury and/or surgery of a leg, it is often recommended that the leg be elevated. Elevating the leg can maximize fluid drainage away from injured tissue and can aid in reducing pain, swelling, and inflammation, which can help the leg to recover faster. Elevating the leg typically involves the patient lying on his/her back and positioning the lower leg above the level of the heart.

Injury and/or surgery of a leg can also result in motion loss. In the case of knee injury and/or surgery, the loss of full knee extension is a particular problem. The inability to fully extend the knee can lead to abnormal joint motion and scar tissue formation in the knee joint. Thus, a goal of post-operative and/or post-injury care is to regain the ability to properly extend the knee. Failure to regain knee extension can lead to complications such as arthritis, continuing knee pain, and weakness in the quadriceps.

BRIEF SUMMARY

Described herein are leg support devices capable of selectively providing different levels of knee extension to a patient. Some embodiments are configured to be moveable between an assembled (or "rest") configuration and a detached (or "therapy") configuration. In the assembled configuration, the support device provides an inclined surface for supporting an elevating the patient's lower leg, knee, and at least a portion of the upper leg. The support device may also include an ankle depression where the patient can position his/her ankle.

When the ankle is positioned in the ankle depression, the ankle and heel are supported and raised but the knee is suspended so as to provide a greater degree of knee extension and stretching. In the detached configuration, the section of the support device including the ankle depression may be separated from the other section to reduce the overall length and height of the used portion of the device and to thereby reduce obstructions and/or make it easier to perform therapeutic motion exercises while the knee is suspended.

In one embodiment, a support device includes a proximal section with an inclined upper surface and a distal section with an inclined upper surface. Each of the proximal section and distal section include attachment features that allow the sections to be selectively attached to one another and detached from one another. When assembled together, the inclined upper surfaces of the proximal section and the distal section form a single, continuous inclined upper surface. The proximal and distal sections may also each include, on their respective upper surfaces, depressions that form a leg depression when the proximal section and the distal section are attached to one another.

Some embodiments may also include a heel depression positioned within the ankle depression. The heel depression sits lower than the rest of the ankle depression so that when the patient positions his/her ankle within the ankle depression, the heel can sink into the relatively lower heel depression and allow the rest of the ankle to seat directly against the ankle depression with a more conforming fit.

An ankle depression may be included in the proximal section, the distal section, or both. In some embodiments, the section(s) including an ankle depression also include a friction-reducing component on its bottom surface to make sliding of the support easier during therapeutic motion exercises.

BRIEF DESCRIPTION OF THE DRAWINGS

To further clarify the above and other advantages and features of the present disclosure, a more particular description will be rendered by reference to specific embodiments illustrated in the appended drawings. It is appreciated that these drawings depict only illustrated and exemplary embodiments of the disclosure and are therefore not to be considered limiting of its scope. Exemplary embodiments of the disclosure will be described with additional specificity and detail through the use of the accompanying drawings in which.

DETAILED DESCRIPTION

Figure 1:
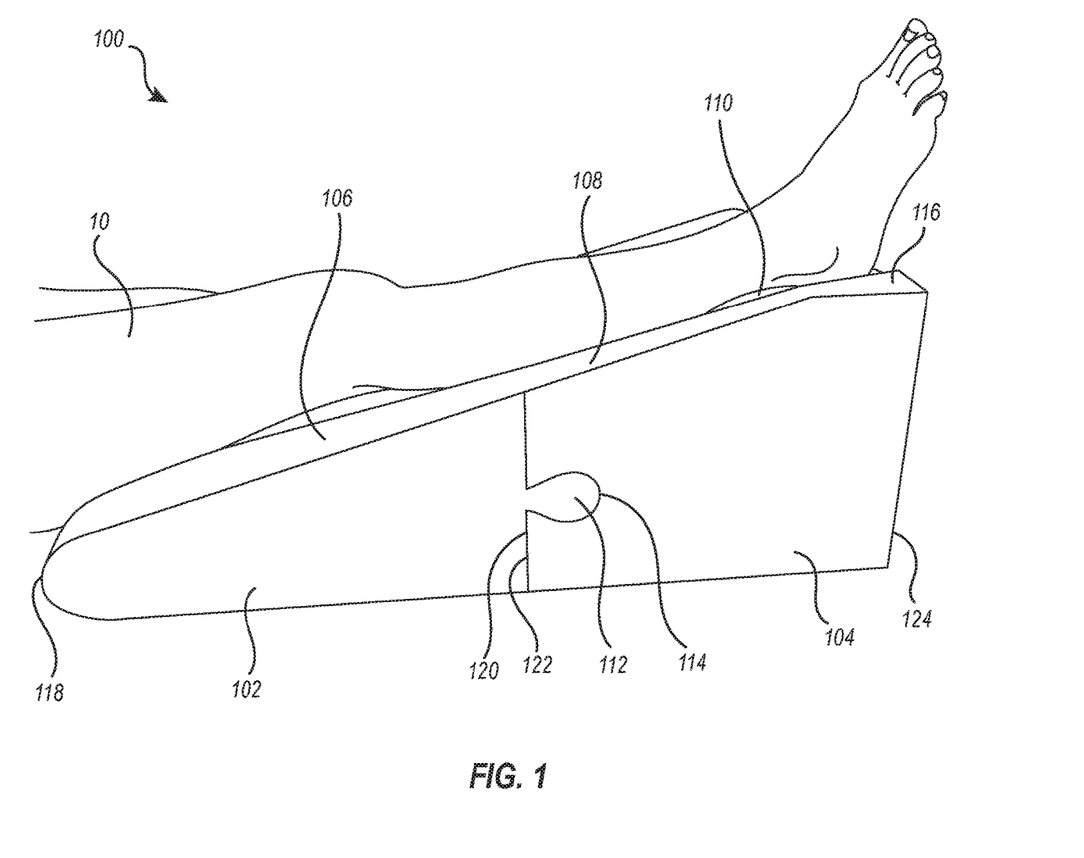
FIG. 1 illustrates an exemplary knee extension device supporting a patient's leg in a rest position, the device supporting a patient's knee and lower leg in an elevated position with the knee extended.

FIG. 1 illustrates an exemplary knee extension device 100 supporting and elevating a patient's leg 10. The knee extension device 100 includes a proximal section 102 and a distal section 104. The separate sections 102 and 104 are attachable to one another to form an assembled or "rest" configuration of the device. In the rest configuration, the device is able to support the leg 10 in a rest position. As shown, the device has a substantially continuous inclined angle that supports and elevates the patient's upper leg, knee, and lower leg. Elevating the patient's leg following injury and/or surgery aids in fluid drainage, reducing swelling, and promoting healing. The illustrated position is suitable during times while the patient is resting.

The proximal section 102 includes an angled surface 106 and the distal section 104 includes a corresponding angled surface 108. The angled surfaces 106 and 108 are matched such that when the proximal section 102 and the distal section 104 are coupled together, the assembled device forms a substantially continuous incline for elevating the patient's leg 10. As shown, the height of the device continuously rises from the proximal end 118 of the proximal section 102 to the distal end 124 of the distal section 104. Other embodiments may have a discontinuous incline, such as one that levels out to some degree distal of a more inclined section. However, preferred embodiments provide a substantially continuous incline in order to better position the leg in a manner that extends the knee when the leg is rested on the device.

When the leg 10 is positioned upon the inclined surface of the device in the illustrated rest position, the force of gravity will tend to cause the knee to move toward the extended position. When the knee has limited mobility, this will aid in passively stretching the leg and promoting greater range of motion and/or better healing.

The proximal section 102 and the distal section 104 are selectively attachable to one another via corresponding attachment features 112 and 114. In the illustrated embodiment, the proximal section 102 includes, at its distal end 120, a distal extension as an attachment feature 112, and the distal section 104 includes, at its proximal end 122, a cavity as a corresponding attachment feature 114. Although the illustrated embodiment positions a distal extension on the proximal section 102 and a cavity on the distal section 104, other embodiments may, in addition to or as an alternative to the illustrated configuration, position a proximal extension on the distal section 104 and a corresponding cavity on the proximal section 102.

The extension and the cavity are adapted to engage with one another with a "puzzle piece" fit. This type of fit provides secure attachment while also allowing for easy detachment by sliding one section laterally relative to the other or by pulling the sections longitudinally apart from one another. Other embodiments may additionally or alternatively include other attachment features, such as corresponding notches and channels, hook and loop fasteners, adhesive or "sticky" surfaces, magnetic attachments, or combinations thereof. Although the illustrated embodiment includes a single pair of corresponding attachment features, other embodiments may include multiple attachment features, such as multiple cavities and multiple corresponding distal extensions.

As explained in greater detail below, the proximal section 102 and distal section 104 are selectively detachable from one another. This allows the device to be moved to a "therapy" configuration (i.e., detached configuration) that allows the patient to readily perform motion exercises and/or more intense knee extension stretches. The therapy position is typically utilized for shorter, more intense rehabilitation sessions while the rest position is typically utilized for longer time periods in between rehabilitation sessions.

The upper surface of the extension device 100 includes a leg depression 110 (underneath the leg 10 in this view) for receiving and conforming to the patient's leg 10. The leg depression 110 aids in supporting the leg 10 and allows the raised edges around the depression to minimize or prevent external rotation of the leg 10. Preventing external rotation also eliminates associated flexion at the knee, further allowing the knee to maintain a desired extended posture. Both the proximal section 102 and the distal section 104 may include shaped depressions that form the full leg depression 110 when coupled together.

The device 100 also includes a plateau portion 116 near the distal end 124 of the distal section 104. The plateau portion 116 is disposed to substantially coincide with the patient's heel when the patient's leg 10 is positioned upon the device. The plateau portion 116 functions to maintain a steady incline along the entire length of the leg 10. Because the heel protrudes posteriorly relative to the ankle, ending the incline just before the heel allows the heel to rest upon the plateau portion 116. This allows more of the calf to touch and be supported by the device rather than be suspended above the upper surface because of the protruding heel. It also allows for better contact against and cradling of the ankle, which is more comfortable to the patient and which beneficially reduces the tendency of the foot to rotate. This helps to keep the foot pointed vertically and better maintains the knee in extension rather than flexion.

Figure 2A:
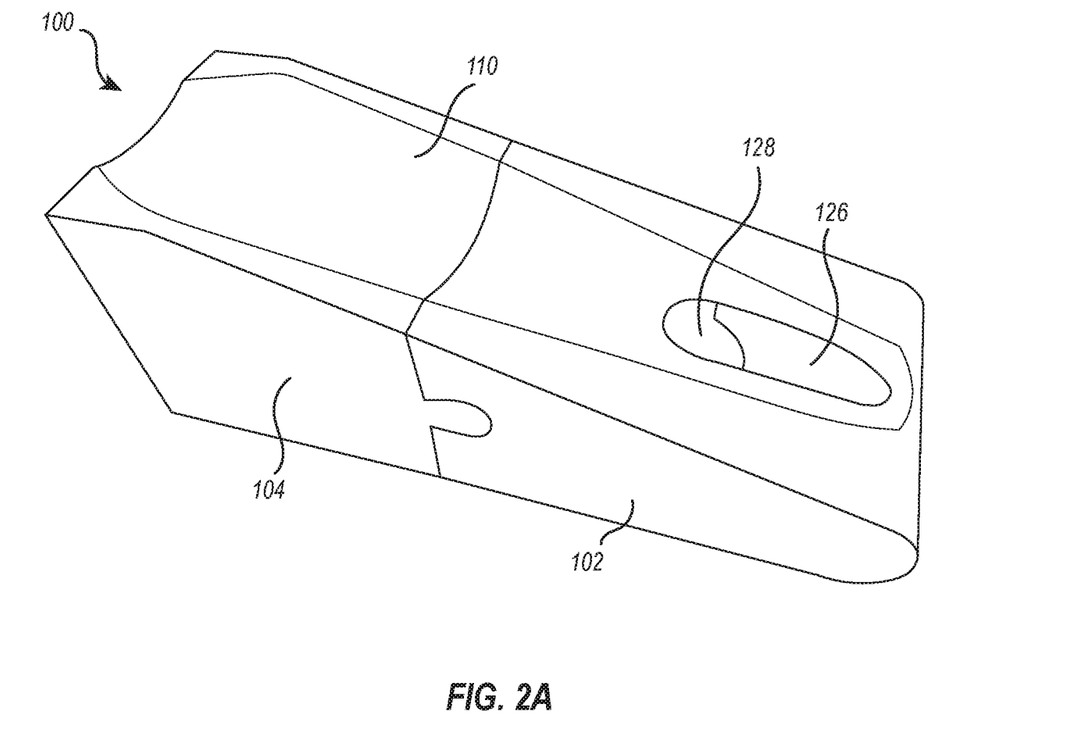
FIGS. 2A and 2B illustrates additional views of the knee extension device of FIG. 1, showing the upper surface with leg depression, ankle depression, and heel depression.
Figure 2B:
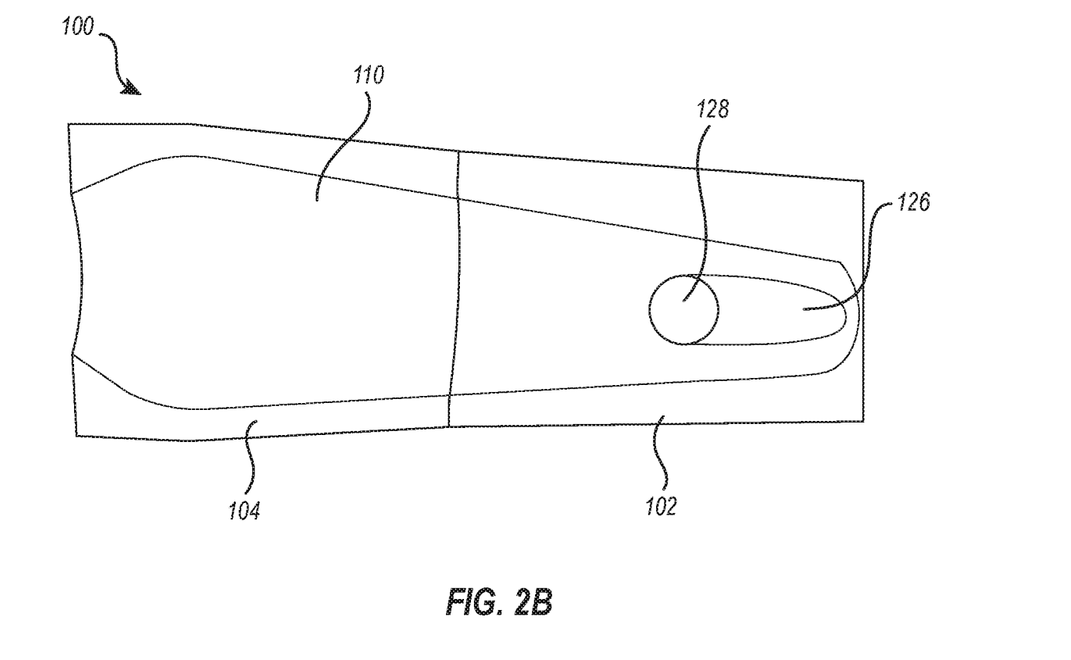

FIGS. 2A and 2B illustrate an isometric view and top view, respectively, of the knee extension device 100. These views also illustrate that the proximal section 102 includes an ankle depression 126 which opens toward the proximal end of the device, and a heel depression 128. The ankle depression 126 and heel depression 128 may be utilized when the device is used to support the patient's leg in a therapy position.

As explained in more detail below, when the patient's leg is positioned in a "therapy" position, the patient's ankle (and in some instances a small part of the lower calf) are supported by the ankle depression 126, while the heel is positioned over the heel depression 128. The heel depression 128 is deeper than the ankle depression 126 and therefore allows the patient's posteriorly protruding heel to sink further down into the device. This also allows the patient's ankle to sink lower and rest directly against the surface of the ankle depression 126, rather than be suspended above the surface because of the posterior protrusion of the heel.

In this particular embodiment, the heel depression 128 is a hole that passes completely through the bottom surface of the device. This beneficially allows the heal to "float" without any pressure points while allowing the ankle and lower calf to sink lower and come into contact with the ankle depression 126. Together, the ankle depression 126 and heel depression 128 function to conform to and securely hold the patient's foot in a vertical position while minimizing or preventing rotation of the leg. As explained above, preventing rotation of the foot is beneficial because rotation tends to mechanically move the knee away from the extended position and into flexion. During therapy, stretching and extending the knee joint is important.

Figure 3:
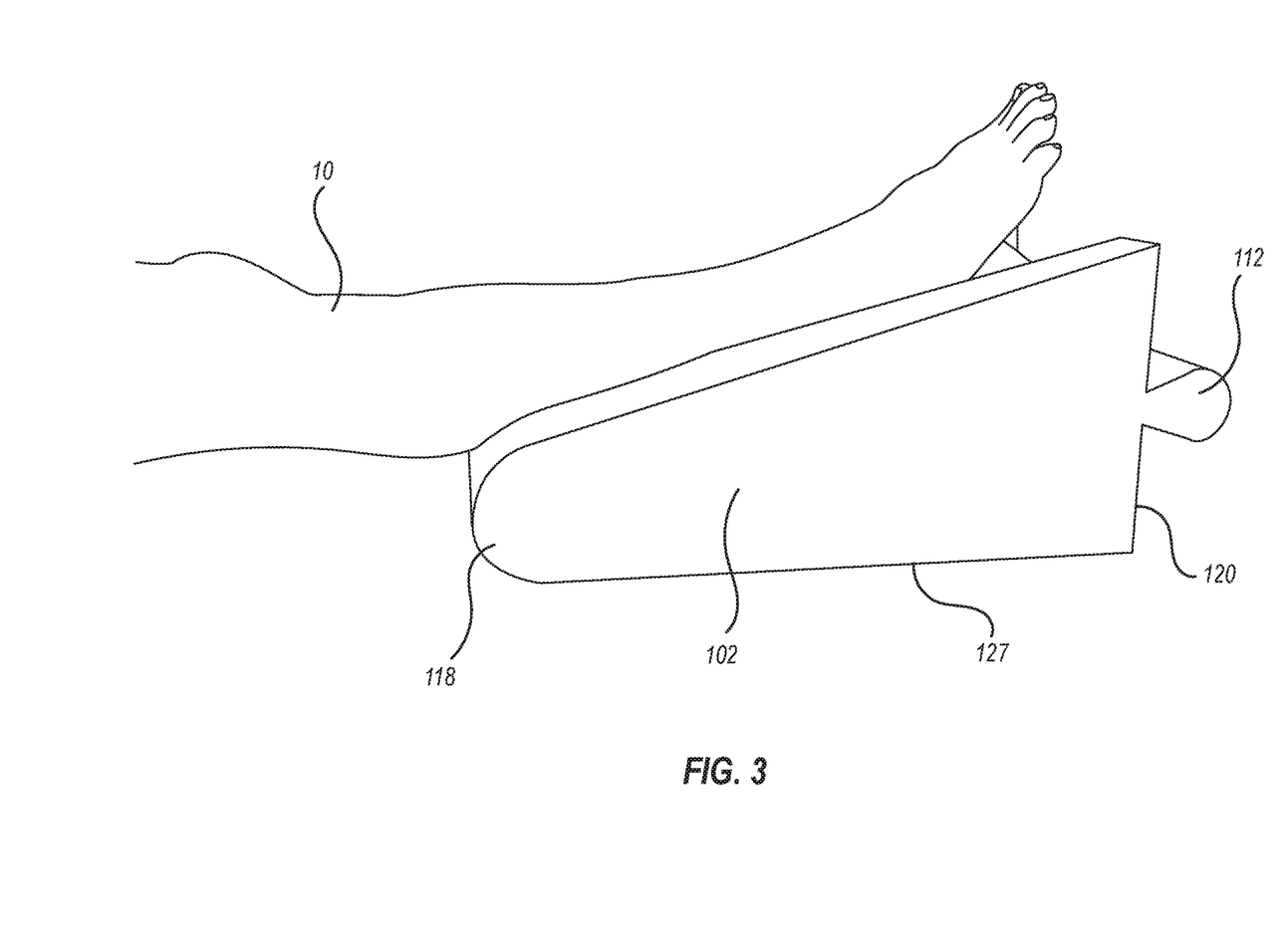
FIG. 3 illustrates the exemplary knee extension device of FIGS. 1 through 2A with the patient's leg in a therapy position, the device supporting and elevating the patient's foot while leaving the knee intentionally suspended and unsupported.

FIG. 3 illustrates the patient's leg supported on the proximal section 102. The device is shown here in the therapy configuration, with the distal section 104 detached from the proximal section 102. Although in some implementations the distal section 104 may remain attached while the patient's leg is positioned within the secondary and heel depressions, the ability to optionally remove the distal section provides several benefits. In many instances, an attached distal extension will stick out too far for any practical use of the proximal section 102 for stretching and/or motion therapy or may make such activities less convenient for the user. For example, an attached distal section would likely stick out and hang over the edge of a bed or table or would abut against an end rail and leave insufficient room to position the leg 10 as desired.

In the therapy configuration, the posterior side of the knee is intentionally suspended rather than supported. This provides a more intense extension stretch to the knee. Typically, this position would not be held for long periods of time (e.g., overnight), but may be utilized for short sessions (e.g., several minutes) as part of therapy or exercise for the knee. By elevating the lower leg while leaving the posterior side of the knee unsupported, the resulting moment force beneficially stretches the knee toward the extended position.

In addition, the shorter and smaller configuration of the device once the distal section has been detached more readily allows the user to perform knee flexion/extension exercises. For example, with the heel supported and the knee suspended as shown, the patient can alternate between flexing the knee to slide the proximal section 102 proximally and extending the knee to slide the proximal section 102 distally. The patient may also move the leg laterally and medially, and/or perform other motion exercises according to an appropriate rehabilitation regimen.

In some embodiments, the bottom surface 127 of at least the proximal section 102 includes a friction-reducing sheet, film, or coating. For example, a thin polymer layer may be sprayed onto the bottom surface or attached via an adhesive or other suitable attachment means. The polymer layer may be made from polypropylene, polycarbonate, polyvinyl, polytetrafluoroethene, nylon, other suitable polymer, or combinations thereof. Regardless of the exact composition, the polymer layer preferably provides a smooth surface with minimal friction. This allows the patient to more easily slide the proximal section 102 around during therapeutic motion exercises.

The proximal section 102 and distal section 104 may be formed of any material suitable for use in physical therapy environments. In preferred embodiments, the separate sections are formed of a foam polymer material. The foam polymer material may optionally be coated with a water-impermeable polymer (e.g., vinyl-based) to protect the foam and provide for easier cleaning. In other embodiments, the device may include a removeable "skin" such as a fabric or sterile sheet material, and may optionally include one or more zippers, hook and loop fasteners, buttons, snaps, and/or other means of donning and doffing the removeable skin. The removeable skin, for example, may be changed from patient to patient and/or from procedure to procedure for sanitary reasons and/or to reduce the amount of cleaning required.

When the knee extension device 100 is in the assembled configuration, the overall length of the device may range from about 2 feet to about 5 feet, or more preferably about 3 feet to about 4 feet. When the separate sections are detached, each section may independently be about 1 foot to about 3 feet long, more preferably about 2 feet long. The angle of the inclined surface of each of the sections may be about 10 to 50 degrees, or about 20 to 45 degrees, or about 30 to 35 degrees. The ankle depression 126 may be formed so that the patient's ankle sits at a height of about 2 to 20 inches, or about 3 to 15 inches, or about 4 to 8 inches (e.g., 5 inches) above the floor-level surface. These heights have been found to be effective for providing sufficient elevation to cause stretching and extension of the knee joint. For example, a height that is too low may not provide sufficient stretching, while heights that are too high may be too uncomfortable for the patient and/or may overly stretch the knee.

Dimensional features within the foregoing ranges beneficially enable the device to support and extend the knee while elevating the leg when in the assembled configuration and to support the ankle while leaving the knee suspended when in the detached configuration. When detached and used for motion exercises and/or more intense stretching, the length of the proximal section 102 is beneficially limited to the foregoing preferred dimensions to allow easier use and mobility of the device.

Figure 4:
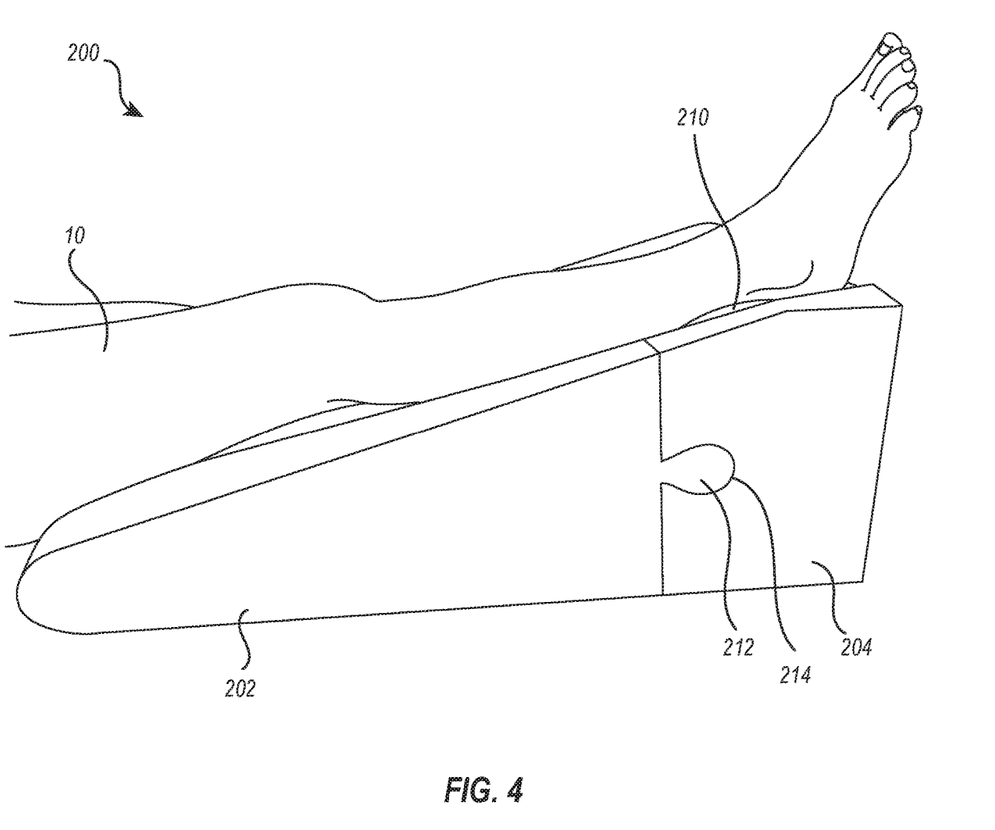
FIG. 4 illustrates an alternative embodiment of a knee extension device wherein the features for supporting the patient's leg in a therapy position are located on the distal section rather than the proximal section.

FIG. 4 illustrates an alternative embodiment of a knee extension device 200. Except as noted below, the knee extension device 200 may include features similar to those of knee extension device 100, including the dimensions, attachment/detachment features, materials, and beneficial uses noted above. As with the knee extension device 100, the illustrated knee extension device 200 includes a proximal section 202, a distal section 204, and a leg depression 210 that extends along the continuous incline formed by the separate sections. The knee extension device 200 may also include attachment features 212 and 214 and/or any of the other attachment feature components described above. A patient's leg may be supported by the assembled device 200 in a resting position, as shown.

Figure 5A:
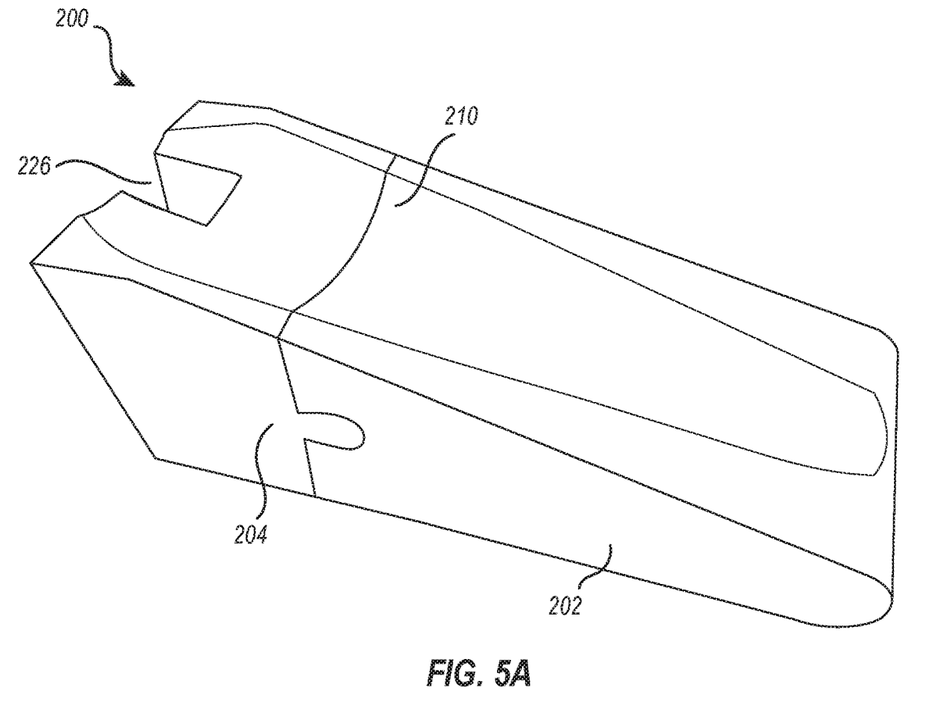
FIGS. 5A and 5B illustrate additional views of the knee extension device of FIG. 4, showing the upper surface with leg depression, ankle depression, and heel depression.
Figure 5B:
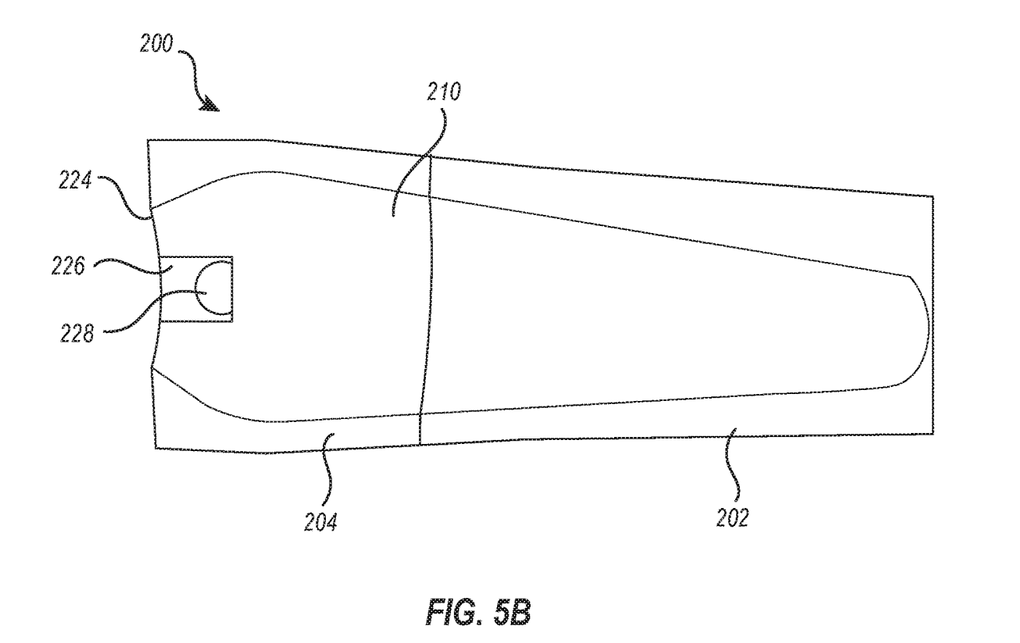

FIGS. 5A and 5B show additional views of the knee extension device 200. In contrast to the embodiment of FIGS. 1 through 3, the illustrated embodiment does not include additional depression features on the proximal section 202. Rather, the distal section 204 includes an ankle depression 226 for supporting the ankle and a heel depression 228 (FIG. 5B) allowing the heel to sink deeper so the ankle can snugly rest against the contour of the ankle depression 226.

Figure 6:
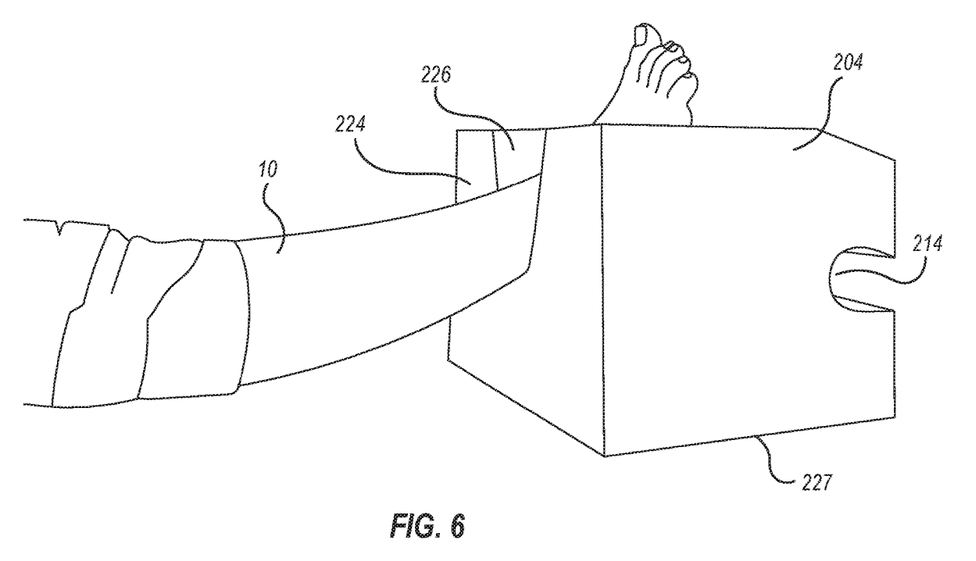
FIG. 6 illustrates the exemplary knee extension device of FIGS. 4 through 5B with the patient's leg in a therapy position, the device supporting and elevating the patient's foot while leaving the knee intentionally suspended and unsupported.

As shown in FIG. 6, the ankle depression 226 opens up toward the distal end of the distal section 204 to define an open end 226. In use, the patient (or medical supervisor or caretaker) can detach the distal section 204 and turn it so that the open end 224 faces proximally rather than distally. The patient's heel can then be placed within the heel depression 228 while the ankle is supported by the ankle depression 226. Then, as with the position shown in FIG. 3, the patient can do passive knee extension stretches and/or motion exercises.

Use of the distal section 204 for supporting the ankle in a therapy position is particularly beneficial. As shown, the ankle depression 226 can be made deep enough to leave side support walls that cradle the sides of the foot and aid in keeping the foot pointed vertically to prevent leg rotation. At the same time, the ankle depression 226 sits high enough that the patient's leg can get sufficient elevation to effectively suspend the knee to promote therapeutic extension and stretching.

The heel depression 228 is likewise beneficial in this regard in that it functions to allow the posteriorly protruding heel to sink further down so that the posterior portion of the ankle can directly contact the upper surface of the ankle depression 226. This can lead to more effective cradling, stability, and support of the foot during therapy.

The lowest point of the ankle depression preferably sits about 2 to 8 inches above the bottom surface 227 of the device (e.g., so that the ankle placed therein sits about 2 to 7 inches above the floor), or more preferably about 2.5 to 7 inches, or about 3 to 6 inches, above the bottom surface 227 of the device. The ankle depression 226 preferably has a depth, as measured from a top surface of the distal section 204, of about 3 to 8 inches, or more preferably about 4 to 6 inches, to provide sufficient cradling of the foot and support of the sides of the foot.

As with the proximal section 102 of the knee extension device 100, at least the distal section 204 of the knee extension device 200 may include a friction-reducing component (e.g., sheet, film, or coating) that allows the patient to slide the distal section 204 along the floor or bed top during therapeutic motion exercises.

Some embodiments may combine features of both the knee extension device 100 and the knee extension device 200. For example, some embodiments may include ankle depression, and optionally heel depressions, in both the proximal sections (as in knee extension device 100) and the distal section (as in knee extension device 200).

The invention claimed is:

1. A modular device configured to provide different levels of knee extension to a patient, the device comprising:
    a proximal section having an inclined upper surface and having an attachment feature at its distal end; and a distal section having an inclined upper surface and having an attachment feature at its proximal end, wherein the attachment feature of the proximal section and the attachment feature of the distal section are adapted to engage with one another to allow selective attachment and detachment of the proximal section and the distal section, the proximal section and distal section forming an assembled configuration when attached and a detached configuration when detached, wherein the inclined upper surfaces of the proximal section and distal section are shaped such that when the proximal section and the distal section are attached, the inclined upper surface of the proximal section and the inclined upper surface of the distal section form a single inclined upper surface inclining upwards from the proximal section to the distal section, wherein the distal section comprises a plateau portion disposed near a distal end of the distal section, the plateau portion having a lower level of incline than the inclined upper surface of the distal section, the plateau portion configured for supporting the patient's ankle and heel when the device is in the assembled configuration, and wherein the proximal section or the distal section includes in its upper surface an ankle depression having an ankle supporting surface that sits at a height lower than the adjacent upper surface on either lateral side, the ankle depression configured for supporting the patient's ankle when the device is in the detached configuration.

2. The device of claim 1, wherein the proximal section and the distal section each include, on their respective upper surfaces, depressions that form a leg depression when the proximal section and the distal section are attached to one another, the leg depression being higher than the ankle depression.

3. The device of claim 1, wherein the attachment features of the proximal section and the distal section are configured to form a puzzle piece fit.

4. The device of claim 1, wherein the proximal section and distal section have lengths such that when in the assembled configuration, the device is capable of supporting the patient's knee and elevating the patient's lower leg and at least a portion of the patient's upper leg.

5. The device of claim 4, wherein the overall length of the device in the assembled configuration is 2 to 5 feet.

6. The device of claim 1, wherein when the device is in the detached configuration, the section including the ankle depression has a length such that it is capable of supporting and elevating the patient's ankle while leaving the patient's knee suspended.

7. The device of claim 6, wherein the section including the ankle depression has a length of 1 to 3 feet.

8. The device of claim 1, further comprising a heel depression disposed within the ankle depression, the heel depression sitting at a lower height than a lowest point of the ankle depression.

9. The device of claim 1, wherein the ankle depression is disposed in the proximal section and opens toward the proximal end of the proximal section.

10. The device of claim 1, wherein the section including the ankle depression also includes a friction-reducing component on its bottom surface.

11. The device of claim 1, wherein the proximal section and the distal section are formed from a polymer foam material.

12. The device of claim 1, wherein the incline has an angle of 10 to 50 degrees.

13. The device of claim 1, wherein a lowest portion of the ankle depression sits at a height of 2 to 8 inches above a bottom surface of the device.

14. The device of claim 1, wherein a lowest portion of the ankle depression sits at a height of 3 to 15 inches above a bottom surface of the device.

15. The device of claim 1, wherein a lowest portion of the ankle depression sits at a height of 4 to 8 inches above a bottom surface of the device.

\* \* \* \* \*